US007085388B2

(12) United States Patent
Butler et al.

(10) Patent No.: US 7,085,388 B2
(45) Date of Patent: *Aug. 1, 2006

(54) HIGH FREQUENCY JET NOZZLE ACTUATORS FOR JET NOISE REDUCTION

(75) Inventors: George W. Butler, Seattle, WA (US); David H. Reed, Kirkland, WA (US); Frederick T. Calkins, Seattle, WA (US); Christopher L. Davis, Kent, WA (US); James H. Mabe, Seattle, WA (US)

(73) Assignee: The Boeing Company, Chicago, IL (US)

( * ) Notice: Subject to any disclaimer, the term of this patent is extended or adjusted under 35 U.S.C. 154(b) by 643 days.

This patent is subject to a terminal disclaimer.

(21) Appl. No.: 10/172,755

(22) Filed: Jun. 14, 2002

(65) Prior Publication Data

US 2003/0231777 A1 Dec. 18, 2003

(51) Int. Cl.
*A61F 11/06* (2006.01)

(52) U.S. Cl. ...................... 381/71.3; 415/119; 60/204; 181/212

(58) Field of Classification Search ............... 381/71.3, 381/71.5, 71.1, 71.7; 60/204; 181/212, 181/241, 224, 206, 217; 415/119
See application file for complete search history.

(56) References Cited

U.S. PATENT DOCUMENTS 3,936,606 A * 2/1976 Wanke .......................... 179/1
4,044,203 A * 8/1977 Swinbanks ................. 381/71.5
5,386,689 A * 2/1995 Bozich et al. ................ 60/803
5,515,444 A * 5/1996 Burdisso et al. ........... 381/71.5
5,732,547 A * 3/1998 Olsen et al. .................. 60/204
5,952,621 A * 9/1999 Curtis et al. ................ 181/213
5,979,593 A * 11/1999 Rice et al. .................. 181/207
6,360,528 B1 3/2002 Brausch et al.
6,718,752 B1 * 4/2004 Nesbitt et al. ................ 60/204

* cited by examiner

*Primary Examiner*—Vivian Chin
*Assistant Examiner*—Lun-See Lao
(74) *Attorney, Agent, or Firm*—Harness, Dickey & Pierce, P.L.C.

(57) ABSTRACT

A noise reduction system for use with an exhaust nozzle associated with a jet engine of an aircraft. The noise reduction system employs a plurality of flow-altering components disposed circumferentially about a lip portion of an exhaust nozzle. In one preferred form the flow-altering components each comprise piezoelectric transduction layers. The flow-altering components are caused to move in an oscillating manner by an AC signal applied thereto such that they move into and out of the exhaust gas emitted from the exhaust nozzle to achieve a desired degree of intermixing of the exhaust flow with the flow adjacent the exhaust nozzle. This produces a reduction in the noise generated by the jet engine. The noise reduction can be utilized during takeoff conditions of an aircraft. The flow-altering components are maintained out of the exhaust gas flowpath during cruise conditions of the aircraft so as not to cause a reduction of thrust, that would in turn result in an increase in the fuel burn during cruise conditions.

17 Claims, 3 Drawing Sheets

HIGH FREQUENCY JET NOZZLE ACTUATORS FOR JET NOISE REDUCTION

FIELD OF THE INVENTION

The present invention relates to noise reduction systems for jet engines, and more particularly to a noise reduction system having a plurality of deployable flow-altering components which can be deployed at selected times of operation of a jet engine to thereby reduce the noise generated by the engine.

BACKGROUND OF THE INVENTION

With ever increasingly stringent noise reduction requirements at airports, noise reduction systems for use with jet engines on private and commercial aircraft are becoming increasingly important. The turbulent mixing of primary-secondary and/or secondary-ambient streams is essentially what produces the broadband jet noise emitted from a jet engine. Takeoff conditions are particularly important since the emitted noise power levels increase with increasing velocity difference between the mixing streams.

Present day noise reduction systems used on commercial aircraft typically involve some form of stationary (i.e., static or fixed geometry) devices, which are often referred to in the industry as “chevrons” or “lobe-mixers”. These fixed devices are typically employed at a downstream edge of an exhaust nozzle and formed so that they protrude into the flow path of the exhaust gas emitted from the jet engine. This causes an intermixing of the exhaust gas with the airstream adjacent the exhaust nozzle. This intermixing serves to reduce the broadband noise generated by the jet engine over a wide range of operating conditions.

The drawback with the above-described, present day chevrons is that such devices, being fixed in their positions, protrude into the exhaust flow at all times during operation of the jet engine. This, of course, generates drag and a loss of thrust. This is important because noise reduction is typically needed only during takeoff of an aircraft and not during cruise conditions. Thus, with present day noise reduction systems that employ fixed chevrons or other like fixed elements, a tradeoff occurs between the needed noise reduction and the desire to avoid the loss of thrust during cruise conditions. As will also be appreciated, noise reduction systems employing fixed chevrons or other like elements which cannot be moved out of the flow path of the exhaust gasses of a jet engine will result in increased fuel burn during cruise operations, thus contributing to increased operating expense for the given aircraft.

It would therefore be highly desirable to provide a noise reducing system for a jet engine used on an aircraft that incorporates a plurality of flow-altering components that can be placed in the flow path of the exhaust flow created by the jet engine during a takeoff condition, but which can be readily retracted out of the flow path once the aircraft reaches a cruise condition. A noise reduction system employing chevrons or other like elements that could be designed to move in a manner that drives disturbances that are closely coupled to the naturally unstable frequencies of the mixing process would be highly desirable in enhancing the initial mixing of the streams without generating large-scale fluid motion. Such a noise reduction system would provide the desired degree of noise reduction during takeoff conditions but would not negatively affect the thrust generated by the engine during cruise conditions, and thus would not negatively impact the amount of fuel required for a given flight.

SUMMARY OF THE INVENTION

The present invention is directed to a noise reduction system employing a plurality of deformable flow-altering components that are disposed adjacent a downstream edge of an exhaust nozzle of a nacelle which houses a jet engine. In one preferred form, the flow-altering components comprise a plurality of transduction actuator elements that are deformable (i.e., deployable) in response to the application of an electric current thereto. In a preferred embodiment, an alternating current is applied to the transduction actuators to cause an oscillating motion. The oscillating motion causes the transduction actuators to effectively oscillate into and out of the flow path of the exhaust gas emitted from the jet engine. When no noise reduction is needed, the electric current applied to the transduction actuators is removed and the actuators remain out of the exhaust gas flow path. In this manner, the transduction actuators do not negatively affect the thrust of the engine, and thus do not result in increased fuel burn of the engine. It is anticipated that the transduction actuators will be employed primarily during takeoff conditions and will remain inoperable (i.e., not deployed) during cruise conditions of an aircraft.

In a preferred embodiment the transduction flow-altering components are configured to extend circumferentially around the entire lip portion of the exhaust nozzle. Each of the flow-altering components may comprise a variety of shapes, but in one preferred form they comprise curved surfaces of rectangular platform which project from the lip portion generally parallel to the exhaust gas flow path when the elements are not being excited with an electrical current. Electrically exciting the flow-altering components causes the desired oscillating motion and, consequently, the desired degree of noise reduction needed at a given time during operation of the jet engine. In the preferred embodiments at least one electrical conductor, and more preferably a plurality of such electrical conductors, are provided which extend through bores or channels in the nacelle to the flow-altering components.

Advantageously, the noise reduction system of the present invention does not significantly complicate the construction of the nacelle nor significantly add to the overall cost of an aircraft, nor require significant additional subsystems to be employed on the aircraft.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
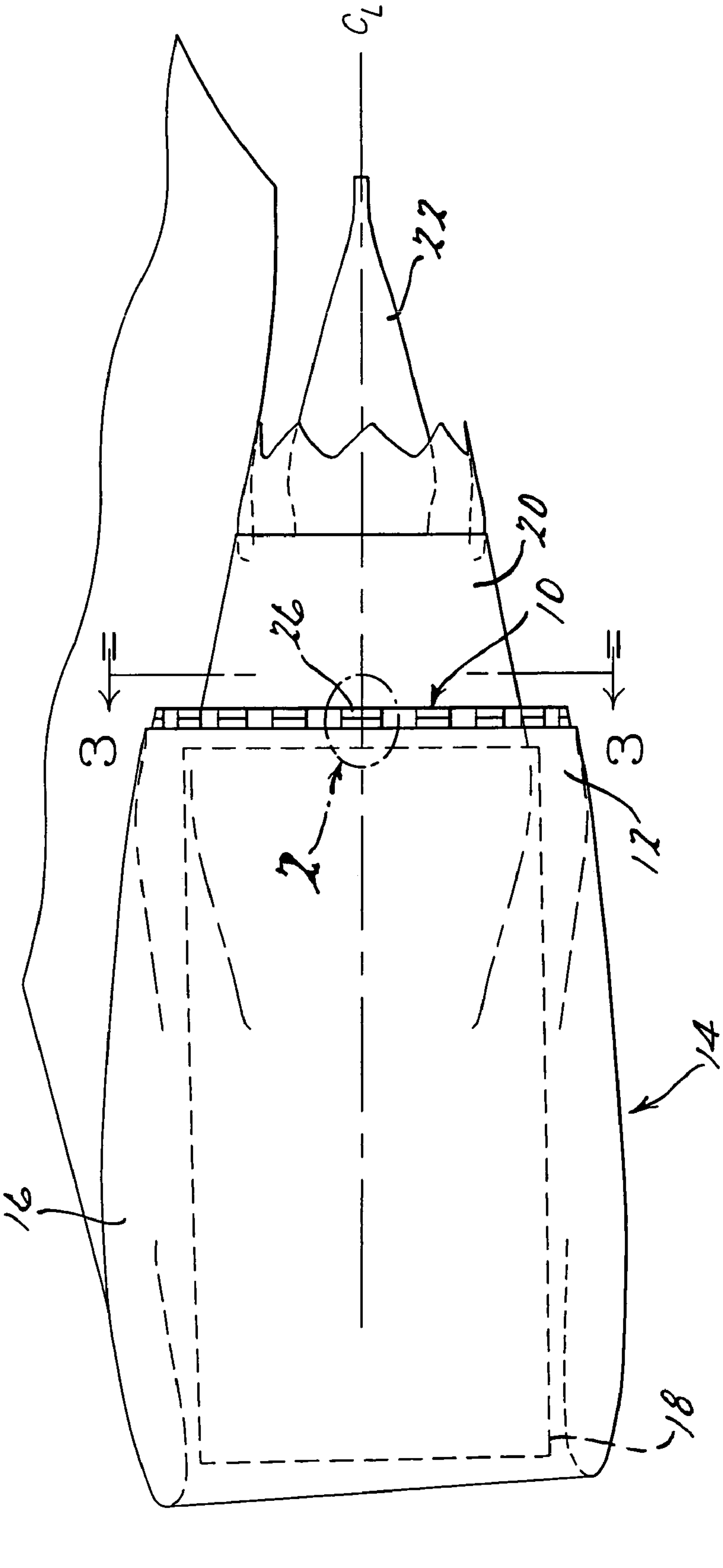
FIG. 1 is a simplified side view of a nacelle incorporating a noise reduction system in accordance with a preferred embodiment of the present invention.

Referring to FIG. 1, there is shown a noise reduction system 10 formed at a lip portion 12 of a secondary exhaust nozzle 16 of a nacelle 14. The nacelle 14 houses a jet engine 18 and also may or may not include a plug 22, which protrudes from a primary exhaust nozzle 20. The nacelle 14, in this example, is coupled to an undersurface of a wing 24 of an aircraft. It will be appreciated immediately, however, that the point of attachment of the nacelle 14 to the aircraft is not germane to the functioning of the noise reduction system 10 and that the noise reduction system can be employed with nacelles that are attached at other areas of an aircraft, such as along an aft portion of the fuselage.

Also, while the noise reduction system 10 is shown on the lip portion 12 of the secondary exhaust nozzle 16, it will be appreciated that the system of the present invention could just as readily be employed on the primary exhaust nozzle 20.

With further reference to FIG. 1, the noise reduction system 10 includes a plurality of flow-altering components 26 extending from the lip portion 12. The flow-altering components 26 are illustrated as rectangular shaped elements, but it will be appreciated that other platform shapes such as triangles, trapezoids, semi-circular projections, or other variously shaped elements could be employed. The flow-altering components 26 are preferably disposed such that they extend generally parallel to the exhaust flow exiting from the secondary nozzle 16 when they are not deployed. When they are deployed, each of the flow-altering components 26 deform or bend such that they project into the flow path of the exhaust gasses emitted from the secondary nozzle 16. The principal feature of the noise reduction system 10 of the present invention, as will be explained more fully in the following paragraphs, is that the flow-altering components 26 are made to oscillate at a desired frequency when they are deployed. This controls the mixing of the exhaust gasses with the airstream flowing adjacent the nacelle 14 by generating a flow disturbance of a preferred scale, and helps to reduce the average jet velocity, thereby reducing the noise produced by the exhaust gas flow stream.

Figure 3:
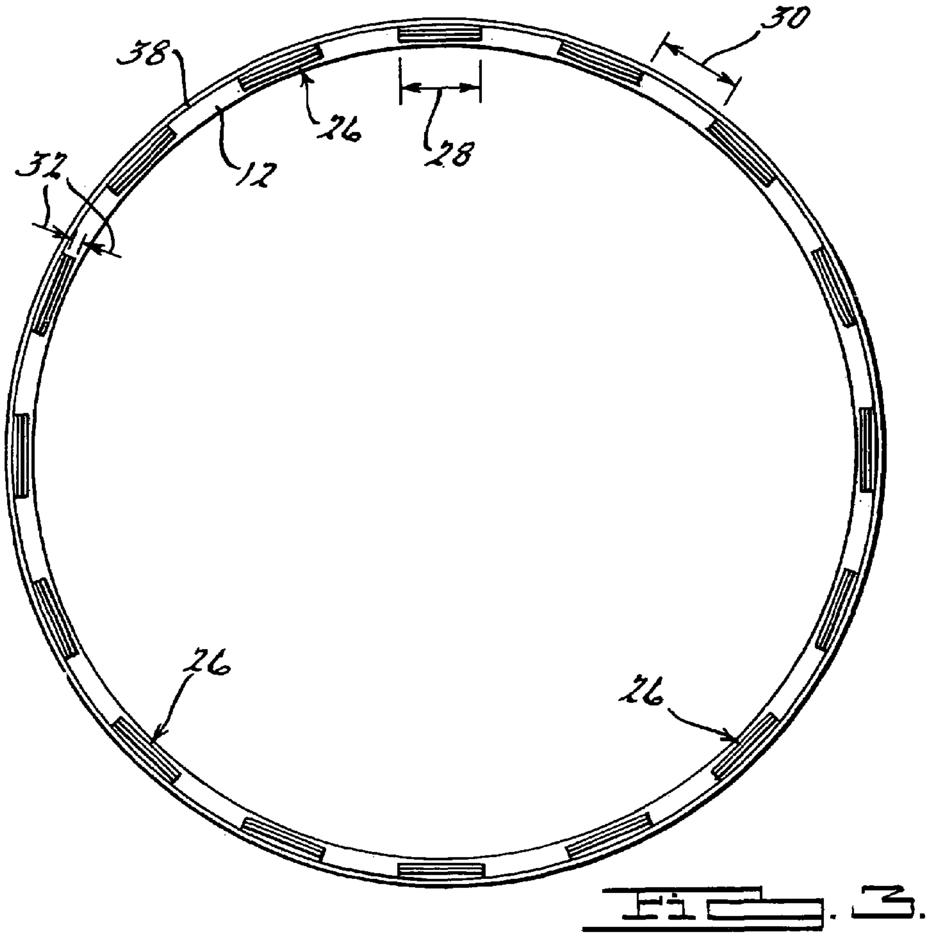
FIG. 3 is an end view of the nacelle of FIG. 1, with the engine being omitted, illustrating more fully the circumferential arrangement of the flow actuating components of the noise reduction system.

With reference to FIGS. 1 and 3, the flow-altering components 26 are preferably arranged circumferentially around the entire circumference of the lip portion 12 of the secondary exhaust nozzle 16. While the width and spacing of the flow-altering components 26 may vary considerably, in one preferred form the width of each flow-altering component 26 is preferably between about 8 inches–12 inches, and more preferably about 10 inches, as indicated by dimensional arrow 28 in FIG. 3. The spacing between adjacent flow actuating components 26, in one preferred form of the present invention, is preferably about equal to the width of one flow actuating component 26, and therefore preferably in the range of about 8 inches–12 inches. This spacing is indicated by dimensional arrows 30. The thickness of each flow-altering component 26 may also vary significantly, but in one preferred form is between about 0.125 inch–0.5 inch (0.3175 mm–12.7 mm), and more preferably between about 0.125 inch–0.250 inch (0.3175 mm–6.35 mm), as indicated by dimensional arrows 32. All of the above-described dimensions could be varied to suit the needs of a specific application.

Figure 2:
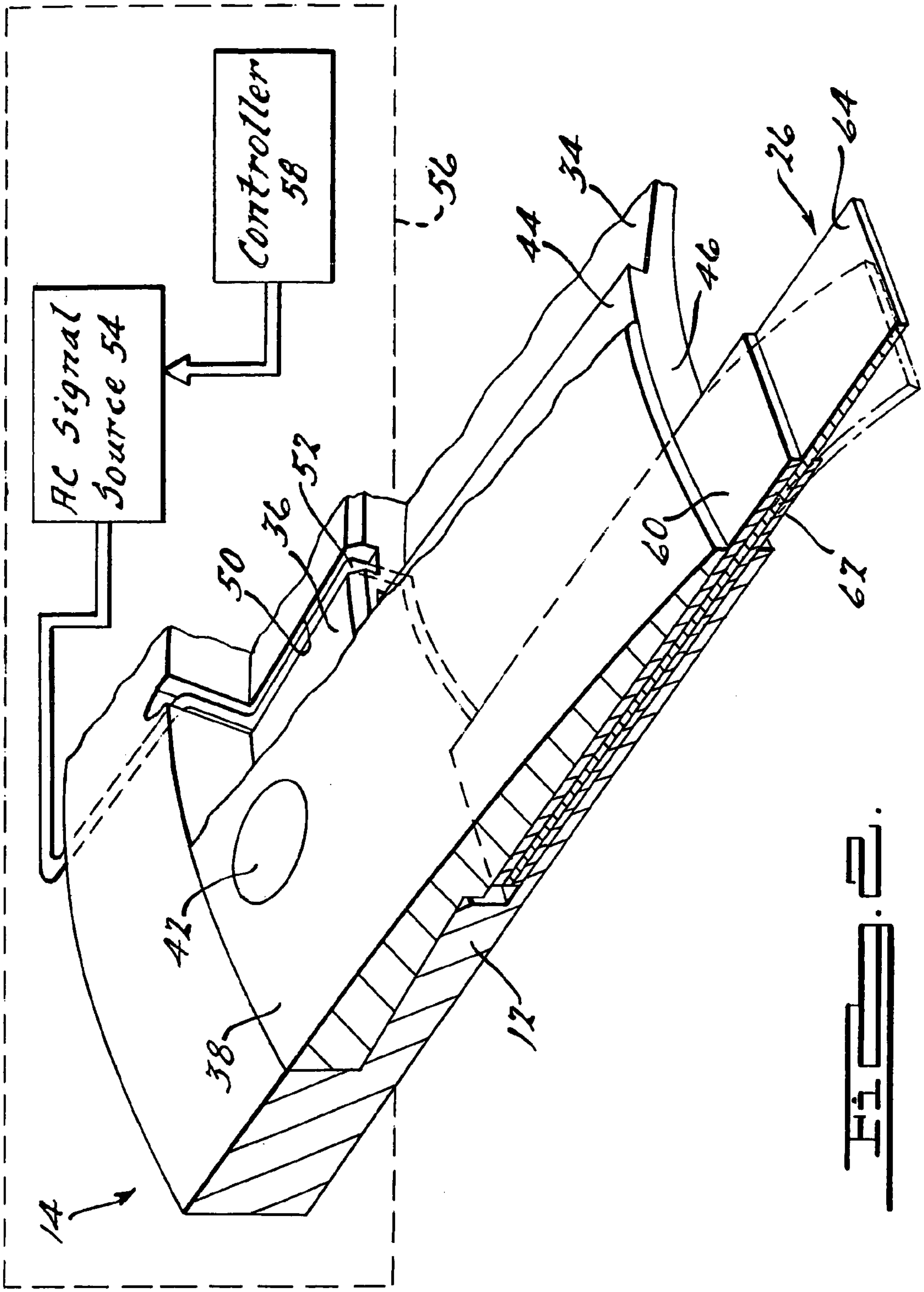
FIG. 2 is a perspective view of a portion of the noise reduction system shown in FIG. 1 in accordance with circled area 2.

Referring now to FIG. 2, the construction of one of the flow-altering components 26 can be seen in greater detail. The lip portion 12 of the secondary exhaust nozzle 16 includes a first notched portion 34 and a second notched portion 36. A circumferential support ring 38 having a notched portion 40 shaped in accordance with notched portion 36 is secured to the lip portion 12 via a plurality of fasteners 42 at a desired number of positions about the circumference of the support ring 38. The precise number of fasteners needed may vary considerably. The fasteners 42 may comprise rivets or other elements suitable for fastening the support ring 38 to the lip portion 12. Additionally, adhesives could be used to secure the support ring 38 to the lip portion 12 either solely or in connection with fasteners 42.

Disposed between the support ring 38 and notched portion 34 of the lip portion 12 are the flow-altering components 26. As mentioned herein, each flow-altering component 26 is formed by transduction material that bends or deflects in response to an electric current applied thereto. In one preferred form, the transduction material comprises piezoelectric material. It will be appreciated, however, that other types of material such as, for example, magnetostrictive material, could also be employed as the transduction material. Accordingly, it will be understood that while piezoelectric material is especially well suited for use as the transduction material, that the present invention is not limited to the use of only piezoelectric material.

With further reference to FIG. 2, adhesives could be used inbetween surfaces of the flow-altering component 26 and the support ring 38 and/or the notched portions 34 to further assist in securing the flow-altering components to the lip portion 12. The portion of each flow-altering component 26 that extends from an edge 46 of the lip portion 12 may vary considerably to suit the needs of a specific application. However, in one preferred form this distance is about 8 inch–12 inch (203 mm–305 mm). The degree of deflection of the flow-altering component 26 needed to achieve the desired mixing of the exhaust flow gasses with the adjacent flow stream as typically between about 0.5 inches–1.5 inches (12.7 mm–38.1 mm). The flow-altering component 26 is shown in its deployed position in dashed lines **26*a* in FIG. 2**.

Referring further to FIG. 2, the lip portion 12 includes a notch 50 for providing a path for at least a pair of electrical conductors represented in simplified form by cable 52. The conductors 52 are in communication with an AC signal source 54 carried on board the aircraft, which is designated in simplified form by dashed line 56. The AC signal source is controlled by a suitable controller 58, also carried on board the aircraft 56. The conductors 52 extend into contact with the flow-altering component 26 and serve to conduct an alternating current (AC) signal to the flow-altering component 26. The AC signal causes an oscillating motion of the transduction flow-altering component 26 to effect the needed intermixing of exhaust flow with the flow stream adjacent the secondary exhaust nozzle 16.

The frequency, phase and amplitude of the signals applied to the flow-altering components 26 may be varied considerably to suit specific applications, since flow instabilities are influenced by each of these factors. In particular, frequency and amplitude set the growth rate of the instability; phase determines the larger scale flow mode or type. The mixing (shear) layers have axial and azimuthal instability modes (and likely others). Different azimuthal modes can be excited by changing the phase of the individual flow-altering components 26 along the circumference of the lip portion 12. For example, if 12 flow-altering components $\mathbf{26}_1$–$\mathbf{26}_{12}$ are used, each flow-altering component could be staggered in phase by 30 degrees from its two adjacent flow-altering components. With respect to flow-altering component $\mathbf{26}_1$, flow-altering component $\mathbf{26}_2$ would be at a phase angle of 30 degrees, flow-altering component $\mathbf{26}_3$ would be at a phase angle of 60 degrees, flow-altering component $\mathbf{26}_4$ would be at a phase angle of 90 degrees, etc. This arrangement of phase angles would drive the layer in mode 1 or the principal "swirling mode". If flow-altering components $\mathbf{26}_1$–$\mathbf{26}_6$ were at a phase angle of 0 degrees and flow-altering components $\mathbf{26}_7$ to $\mathbf{26}_{12}$ were at a phase angle of 180 degrees, this would drive a side-to-side motion or a "flapping mode". If the phase between the flow-altering components 26 is 0 degrees, then only the axisymmetric mode will be driven. This does not mean that this mode is the only one that will exist; one mode can be overcome by another as a fluid element moves downstream. As will be appreciated, there are a plurality of other combinations that could exist. Ideally, one would like to couple to the dominant modes of the flow that the system 10 is trying to influence.

Amplitude is principally important because the frequency and mode of the instability that is excited should be more energetic than other competing instabilities. To alter the growth rate or change the mixing rate of the shear layer, the excitation signal should first be coupled in frequency and phase.

The frequency at which the flow-altering components 26 are caused to oscillate will thus preferably be such that couple with the instability of the initial mixing layer, thus altering the initial turbulence scales, increasing the mixing rate, and reducing the average step velocity. These instabilities can be represented by Strouhal numbers ($S_t$) on the order of 0.3, where $S_t$ equals FD/$U_j$. The variable "F" represents the frequency, "D" represents the nominal dimension (e.g., jet diameter), and "$U_j$" is the velocity of the jet. For example, the frequency of the most unstable mode of a 30 inch (76.2 cm) diameter, 1000 ft/second jet would be on the order of 120 Hz. This represents the lower bound of the flow-altering component 26 frequency range. In practice, however, considerably higher driving frequencies may be employed (e.g., 1 to 10 KHz) to effectively couple with the initial mixing layer.

It is a principal advantage of the present invention that when no noise abatement is needed, the flow-altering components 26 can be allowed to return to the position shown in solid lines in FIG. 2. This position represents a "neutral" or minimum loss condition relative to the thrust produced by the jet engine 18. The neutral position may, in effect, form a simple continuation of the lip portion 12 so that the flow-altering component 26 extends parallel to the lip portion 12, or it may comprise a position in which the flow-altering component 26 extends slightly non-parallel to the lip portion 12, either slightly towards or away from the exhaust flow stream exiting the secondary exhaust nozzle 16. It is anticipated that the neutral position will be the position used during cruise conditions and that the flow-altering components 26 will need to be deployed primarily during takeoff of an aircraft. There is no restriction on the direction of the travel of the flow-altering components 26. For example, an outermost tip 26*b* (26*b* not shown in the figure) of the flow-altering components 26 shown in FIG. 3 could be made to oscillate between primary and secondary exhaust streams emitted from the nacelle 14.

Figure 4:
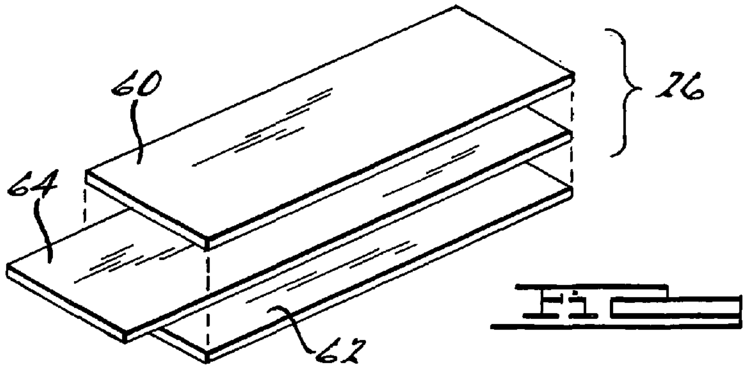
FIG. 4 is an exploded perspective view of the construction of one flow-altering component.

Referring now to FIG. 4, the construction of one preferred form of the flow-altering component 26 is shown. The flow-altering component 26 comprises transduction layers 60 and 62 with a metal layer 64 sandwiched therebetween. Suitable adhesives, such as DP-8005 from the 3M Company may be employed for this purpose. Metal layer 64 may comprise steel or any other suitable material for providing support to the transduction layers 60 and 62. Component 64 can extend beyond the transduction layers 60 and 62 into the flow if desired, as shown in FIGS. 2 and 4. However, the transduction layers 60 and 62 could also be made the same length as the metal layer 64 if needed to suit a specific application. The thickness of each transduction layer 60 62 is preferably in the range of about 0.02 inch–0.2 inch (0.05 mm–0.5 mm). The thickness of the metal layer 64 may vary considerably but is preferably between about 0.02 inch–0.2 inch (0.05 mm–0.5 mm). When an AC signal is applied to the flow-altering component 26, one of the transduction layers 60 and 62, for example the top layer 60, expands while the bottom layer 62 contracts, thus causing the "bending" of the component 26 into the exhaust gas flowpath. During the next half cycle of the AC signal, the top transduction layer 60 contracts while the bottom layer 62 expands, thus causing movement of the flow-altering component 26 in the opposite direction (i.e., back towards its neutral position). Furthermore, a single transduction layer, either 60 or 62, may be used alone to provide the needed degree of "bending".

The noise reduction system 10 of the present invention thus provides a means for providing a reduction in the noise emitted from an exhaust nozzle associated with a jet engine without increasing the fuel burn of the jet engine when no noise reduction is needed. The noise reduction 10 effects an oscillating motion of each of the flow-altering components 26 of the system 10 to even more effectively control the intermixing of the exhaust gasses emitted from the exhaust nozzle associated with the jet engine during takeoff conditions of an aircraft, while allowing the flow-altering components 26 to be maintained out of the exhaust gas flow path during cruise conditions so as not to negatively affect the thrust generated by the jet engine.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. A noise reduction system for a jet engine housed within a nacelle of an aircraft, comprising:

a plurality of flow-altering components disposed circumferentially about a lip portion of an exhaust nozzle of said nacelle so as to extend adjacent to an exhaust flow emitted from said exhaust nozzle;

each of said flow-altering components including a transduction element adapted to deform in response to an application of an electric current thereto such that each said flow-altering component extends into said exhaust flow, thereby promoting mixing of said exhaust flow with an adjacent flow stream outside of said exhaust nozzle; and a current source for controllably applying an electric current to said transduction element.

2. The system of claim 1, wherein each said flow-altering component comprises:

a pair of said transduction elements; and a layer of metal disposed in between said pair of transduction elements.

3. The system of claim 2, wherein a first one of said pair of transduction elements expands when said electric current is applied thereto, and wherein a second one of said transduction elements contracts when said electric current is applied thereto, thereby causing said flow-altering component to deform and project into said exhaust flow.

4. The system of claim 1, wherein said current source comprises an alternating current source that causes said flow-altering components to move in an oscillating manner generally in accordance with a frequency and phase of said electric current output by said alternating current source.

5. The system of claim 1, wherein said flow-altering components are spaced apart generally evenly about a circumference of said lip portion of said exhaust nozzle.

6. The system of claim 1, wherein said transduction element comprises a layer of piezoelectric material.

7. A noise reduction system for a jet engine housed within a nacelle of an aircraft, comprising:

a plurality of flow-altering components disposed circumferentially about a trailing lip portion of an exhaust nozzle of said nacelle so as to form extensions of said lip portion that extend adjacent to an exhaust flow emitted from said exhaust nozzle;

each of said flow-altering components including:

at least one transduction element adapted to deform sufficiently in response to an application of an electric current thereto such that each said flow-altering component extends, in a first position, into said exhaust flow, thereby promoting mixing of said exhaust flow with an adjacent flow stream outside of said exhaust nozzle, and in a second position generally co-planar with said lip portion so as not to extend into said exhaust flow; and a substrate secured to said transduction element for providing support to said transduction element; and a current source for controllably applying an electric current to said transduction element.

8. The system of claim 7, wherein said substrate comprises a layer of metal.

9. The system of claim 7, wherein each said flow-altering component comprises:

a pair of said transduction elements; and wherein said substrate comprises a metal layer interposed between said transduction elements.

10. The system of claim 7, wherein said current source comprises an alternating current source, and wherein said alternating current generated from said alternating current source causes an oscillating movement of said flow-altering components towards and away from said exhaust flow.

11. The system of claim 10, wherein said flow-altering components oscillate at a frequency generally in accordance with a frequency and phase of said alternating current.

12. The system of claim 7, wherein each said transduction element comprises a piezoelectric layer of material.

13. The system of claim 7, wherein each of said flow altering components form rectangular-like projections extending from said trailing lip portion of said exhaust nozzle.

14. A method for reducing noise emitted from an exhaust nozzle of a jet engine, comprising:

disposing a plurality of flow-altering components circumferentially about a lip portion of exhaust nozzle to extend from said lip portion, wherein each of said flow-altering components deforms in response to an electric current applied thereto so as to project, in a first position, into an exhaust flow emitted from said exhaust nozzle and in a second position to extend generally co-planar with said lip portion; and applying an electric current to said flow-altering components to thereby cause said flow-altering components to deform move from said second position into said first position, to thus project into said exhaust flow, thereby promoting mixing of said exhaust flow with an adjacent air stream outside of said exhaust nozzle to attenuate noise emitted from said exhaust nozzle.

15. The method of claim 14, wherein said step of applying electric current comprises applying an alternating current to cause said flow-altering components to oscillate towards and away from said exhaust flow.

16. The method of claim 14, wherein the step of disposing a plurality of flow-altering components comprises disposing a plurality of piezoelectric, flow-altering components circumferentially about said lip portion.

17. The method of claim 14, wherein disposing said flow altering components comprise disposing a plurality of rectangular-like flow altering components to extend from said lip portion.

* * * * *